United States Patent [19]
Detweilwer

[11] Patent Number: 5,549,122
[45] Date of Patent: Aug. 27, 1996

[54] METHODS OF SURGICAL MAMMALIAN VESSEL ANASTOMOSIS

[76] Inventor: Mark B. Detweilwer, 1 S. Chester Rd., Apt. #4, Swarthmore, Pa. 19081

[21] Appl. No.: 215,387

[22] Filed: Mar. 21, 1994

Related U.S. Application Data

[60] Division of Ser. No. 929,060, Aug. 13, 1992, abandoned, which is a continuation-in-part of Ser. No. 555,343, Jul. 19, 1990, Pat. No. 5,141,516.

[51] Int. Cl.$^6$ .......................... A61B 19/00; A61B 17/08
[52] U.S. Cl. .......................... 128/898; 623/11; 606/151; 606/153
[58] Field of Search .......................... 606/151, 153, 606/154, 213, 214, 215, 216, 218; 128/898; 623/11

[56] References Cited

U.S. PATENT DOCUMENTS

| | | | |
|---|---|---|---|
| 3,771,526 | 11/1973 | Rudie | 606/153 |
| 4,705,039 | 11/1987 | Sakaguchi et al. | 128/334 C |
| 4,883,618 | 11/1989 | Barrows | 606/154 |
| 4,899,744 | 2/1990 | Fujitsuka et al. | 606/153 |
| 5,064,057 | 11/1991 | Iwatsuki et al. | 606/154 |
| 5,141,516 | 8/1992 | Detweiler | 606/153 |
| 5,180,392 | 1/1993 | Skeie et al. | 623/11 |
| 5,185,408 | 2/1993 | Tang et al. | 604/21 |
| 5,209,776 | 5/1993 | Bass et al. | 606/214 |
| 5,250,058 | 10/1993 | Miller et al. | 606/153 |
| 5,282,810 | 2/1994 | Allen et al. | 606/151 |

OTHER PUBLICATIONS

Murphy, J. B., "Cholecysto–Intestinal, Gastro–Intestinal, Entero Intestinal Anastomosis, and Appoximation Without Sutures," *Medical Record*, 42:665–676 (Dec. 10, 1982).

Hardy, T. Jr., et al., "A Biofragmentable Ring for Sutureless Bowel Anastomosis An Experimental Study", *Dis. Colon Rectum*, 28:484–490 (1985).

Hardy, T., Jr., et al., "Initial Clinical Experience with a Biofragmentable Ring for Sutureless Bowel Anastomosis", *Dis Colon Rectum*, 30:55–61 (1987).

Maney, J., et al., "Biofragmentable Bowel Anastomosis Ring: Comparative Efficacy Studies in Dogs," *Surgery*, 103:56–62 (1988).

Cahill, C. J., et al., "Sutureless Large Bowel Anastomosis: European Experience with the Biofragmentable Anastomosis Ring," *Br. J. Surg.*, 76:344–347 (1989).

(List continued on next page.)

*Primary Examiner*—Paul B. Prebilic
*Attorney, Agent, or Firm*—Panitch Schwarze Jacobs & Nadel, P.C.

[57] ABSTRACT

Surgical mammalian vessel anastomosis is accomplished by connecting first vessel and second vessel stumps with generally annular openings using an anastomosis apparatus, having a stent and a stent placement member. The method comprises circumferentially inserting a first and second purse-string suture into the respective first and second vessel stumps, placing the stent member at least partially within the receiving portion of the stent placement member, inserting the stent member and stent placement member through an opening in the second vessel stump remote from the generally annular opening of the second vessel stump until the stent member extends at least partially through the generally annular opening of the second vessel stump, inserting the first end of the stent member into the generally annular opening of the first vessel stump, tightening the purse-string sutures to annularly introflect the edges of the first and second vessel stumps onto the second end of the stent member, and applying a compressive force to the stent member within the receiving portion of the stent placement member to cause the annularly introflected edge of the first vessel stump to engage the annularly introflected edge of the second vessel stump to form a substantially annular engagement region between the stent member and the stent placement member with a clamping force sufficient to retain the edges of the stumps in annular engagement. A biocompatible sealant is applied and cures in minutes before removing the purse-string sutures.

14 Claims, 6 Drawing Sheets

OTHER PUBLICATIONS

Kamiji, T., et al., "Microvascular Anastomosis Using Polyethylene Glycol 4000 and Fibrin Glue," *British Journal of Plastic Surgery,* 42:54–58 (1989).

M. P. Bubrick et al., "Prospective, Randomized Trail of the Biofragmentable Anastomosis Ring," *Am. J. Surg.* 161, pp. 136–142 (1991).

M. L. Corman et al., "Comparison of the Valtrac Biofragmentable Anastomosis Ring with Conventional Suture and Stapled Anastomosis in Colon Surgery," *Dis. Colon Rectum* 32, pp. 183–187 (1989).

C. Rebuffat et al., "Clinical Application of a New Compression Anastomotic Device for Colorectal Surgery," *Am. J. Surg.* 159, pp. 330–335 (1990).

Z. Cong et al., "Experimental Study on Microvascular Anastomosis Using a Dissolvable Stent Support in the Lumen," *Microsurgery* 12, pp. 67–71 (1991).

A. Liboni et al., "AKA–2. A New Introflecting Circular Stapler in Colo-rectal Surgery," *Acta Chir Italica* 41, pp. 536–590 (1985).

Senn, N., "Enterorrhaphy; Its History, Technique and Present Status," *J.A.M.A.,* 21(7):215–35 (1893).

Hjortrup, A. P. et al., "Fibrin Adhesive Versus Sutured Anastomosis: A Comparative Intra-Individual Study in the Small Intestine of Pigs," *Br. J. Surg.,* 73:760–61 (1986).

Ethicon, Inc. brochure entitled "PROXIMATE™ ILS Disposable Intraluminal Stapler System".

METHODS OF SURGICAL MAMMALIAN VESSEL ANASTOMOSIS

CROSS-REFERENCE TO RELATED APPLICATIONS

This is a division of my U.S. patent application Ser. No. 07/929,060, filed Aug. 13, 1992, now abandoned, which in turn was a continuation-in-part of U.S. patent application Ser. No. 07/555,343, filed Jul. 19, 1990, now U.S. Pat. No. 5,141,516, the disclosure of which is incorporated herein by reference.

BACKGROUND OF THE INVENTION

The present invention relates to dissolvable intraluminal stents for mammalian anastomoses.

Surgical anastomosis is the procedure of choice to relieve or correct blocked, diseased or otherwise inoperative luminal vessels. The most common vessel to which this procedure is applied is the intestine, but the procedure may also be used to correct abnormalities in blood vessels, biliary and urinary ducts, for example, as well as other vessels. However, it has been long recognized that there is a need for an essentially sutureless procedure.

As early as 1892, J. B. Murphy reported sutureless anastomosis procedures using what he called an anastomosis button. J. B. Murphy "Cholecysto-Intestinal, Gastro-Intestinal Entero-Intestinal Anastomosis, An Approximation Without Sutures," *Medical Record*, 42(24):665–76 (Dec. 10, 1892). The techniques described by Murphy were adopted by the medical community for several decades and the button became commonly called the "Murphy button." The Murphy button generally comprised a two-part metal clamping device which, when screwed together, would hold the two vessel stumps in close proximity until scar tissue joined the two stumps. However, one major disadvantage was that the button, when used in intestinal anastomosis procedures, would either pass several days after the surgical procedure, causing great discomfort, or would become lodged in the intestinal lumen, causing serious blockage. Blockage could also occur when feces packed the transit canal. In addition, necrosis at the anastomosis site was prevalent when using the Murphy button, sometimes resulting in infection and/or lumen obstruction due to stenosis.

More recently, a sophisticated variant of the Murphy button has been developed and is commonly called the bowel anastomosis ring (BAR). The early work of the BAR was performed and reported by T. G. Hardy et al., "A Biofragmentable Ring for Sutureless Bowel Anastomosis", *Dis. Col. & Rect.*, 28:484–90 (1985), with later work by Hardy and others. T. G. Hardy et al., "Initial Clinical Experience With a Biofragmentable Ring for Sutureless Bowel Anastomosis," *Dis. Col & Rect.*, 30:55–61 (1987); J. W. Maney et al., "Biofragmentable Bowel Anastomosis Ring: Comparative Efficacy Studies in Dogs," *Surgery*, 103(1):56–62 (1988); C. J. Cahill et al., "Sutureless Large Bowel Anastomosis: European Experience With the Biofragmentable Anastomosis Ring," *Br. J. Surg.*, 76(4):344–47 (1989). The BAR functions similarly to the Murphy button by holding two vessel stumps in contact with one another after securing each of the vessel stumps to the BAR with a purse-string suture and snapping the two BAR pieces together.

The BAR is fashioned from a composition that fragments under normal intraluminal conditions and these BAR fragments are usually expelled about two to three weeks after implantation. However, these fragments are irregular, generally several millimeters to over 2 centimeters in length, thereby causing discomfort when passed. Other complications include the premature breaking away of the whole BAR from its site with the possibility of compromising the anastomosis and having to pass the intact device. The BAR cannot be installed above an intact ileocecal valve since the fragments could obstruct or tear the valve. Moreover, in the descending colon, the BAR may become obstructed by feces and cause signs of low bowel obstruction which usually pass when the BAR fragments, but this commonly prolongs the hospital stay of the patient. This problem is exacerbated when the BAR is situated lower in the descending colon and sigma where the feces are increasingly denser, resulting in a corresponding increased tendency to plug the canal for intestinal contents to transit through the BAR before it fragments.

In addition, the BAR anastomosis procedure requires that purse-string sutures be inserted and tied and must remain in the vessel stumps to attach these stumps to the BAR after the surgical procedure has been completed. These sutures may remain in the vessel tissue for several days to several weeks and their presence, in addition to the pressure of the BAR clamping the two stumps together, increases the risk of edema, ischemia, infection, necrosis and perforation. Moreover, despite efforts to decrease this necrosis at the anastomosis, primarily accomplished by providing the BAR with interdigitating parts which lock at various gap sizes, necrosis may still occur at the site of purse-string sutures following the BAR procedure. Since the selection of gap sizes is limited and the gap distances are relatively narrow, it is possible that the vessel stumps may be too thick to be inserted into the BAR before closing. Also, when the thickness of the stumps are nearly equal to the gap size, closing the BAR causes an increase in vascular damage, resulting in edema and consequent problems, such as ischemia, necrosis and micro- or macronecrosis and perforation and thus, causing minor or major leakage of intestinal or vessel contents into body cavities.

In addition, using conventional BAR and other suturing devices in hard to reach places, such as the low rectum or esophagus, it is particularly difficult to position the device for desired placement and clamping effects.

Still further, sucrose base stents which dissolve are particularly fragile, tending to break or fracture during anastomosis procedures, rendering them useless and in need of replacement to complete the surgical procedure.

The present invention overcomes the inefficiencies and deficiencies of the prior art by virtue of an improved anastomotic stent and placement device for anastomosis procedures which is believed to be more reliable in most uses, simplifies the surgical procedure, and may lessen the surgical complications and postoperative discomfort to the patient, in addition to shortening the hospital stay.

SUMMARY OF THE INVENTION

According to one aspect of the present invention, a stent for receiving a vessel stump for mammalian anastomoses comprises a dissolvable member made of a biocompatible, non-toxic material which substantially completely dissolves in mammalian bodily fluids and having reinforcing means extending at least partially therethrough.

Another aspect of the present invention is an apparatus for mammalian anastomoses comprising a stent member for receiving a first vessel stump, the stent member having a first end with a first circumference and a second end with a second circumference smaller than the first circumference, the stent member being made of a biocompatible, non-toxic material which substantially completely dissolves in mammalian bodily fluids, and a removable stent placement member for insertion through a second vessel stump, the stent placement member having an outer circumference substantially the same as the first circumference of the stent member and having a receiving portion with an inner circumference for at least partially receiving the second end of the stent member, the stent member and the receiving portion of the stent placement member being substantially axially aligned when the second end of the stent member is received by the stent placement member.

Preferably, the apparatus comprises a connecting member secured to the stent member and compression retaining means attached to the stent placement member and functionally attached to the connecting member for applying and holding a compressive force for retaining the second end of the stent member at least partially within the receiving portion of the stent placement member.

Yet another aspect of the present invention is a method of surgical mammalian vessel anastomosis connecting a first vessel stump having a generally annular opening to a second vessel stump having a generally annular opening using the anastomosis apparatus comprising the steps of circumferentially inserting a first purse-string suture into the first vessel stump and a second purse-string suture into the second vessel stump where the first and second purse-string sutures are positioned proximate the edges of the first and second vessel stumps, placing the stent member at least partially within the receiving portion of the stent placement member, inserting the stent member and stent placement member through an opening in the second vessel stump remote from the generally annular opening of the second vessel stump until the stent member extends at least partially through the generally annular opening of the second vessel stump, inserting the first end of the stent member into the generally annular opening of the first vessel stump, tightening the purse-string sutures to annularly introflect the edges of the first and second vessel stumps onto the second end of the stent member, and applying a compressive force to the stent member within the receiving portion of the stent placement member to cause the annularly introflected edge of the first vessel stump to engage the annularly introflected edge of the second vessel stump to form a substantially annular engagement region between the stent member and the stent placement member with a clamping force sufficient to retain the edges of the stumps in annular engagement.

BRIEF DESCRIPTION OF THE DRAWINGS

The foregoing summary of the invention, as well as the following detailed description of preferred embodiments will be better understood when read in conjunction with the appended drawings. For the purpose of illustrating the invention, there is shown in the drawings embodiments which are presently preferred, it being understood, however, that the invention is not limited to the specific arrangements and instrumentalities disclosed. In the drawings.

DETAILED DESCRIPTION OF PREFERRED EMBODIMENTS

Figure 2:
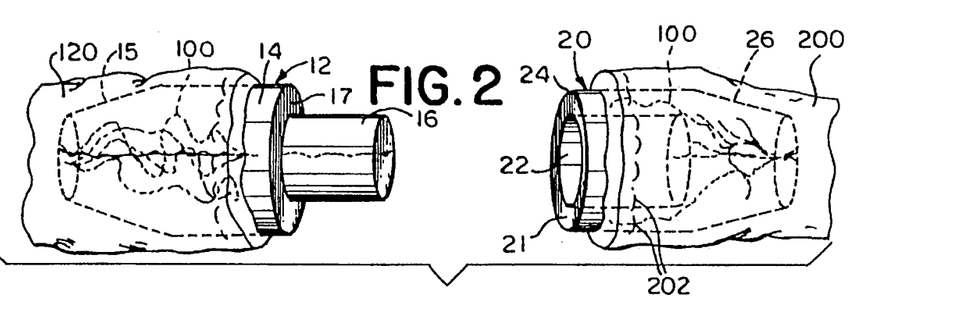
FIG. 2 is a side elevational view of two vessel stumps having male and female members of a dissolvable stent according to the present invention inserted therein.
Figures 3A, 3B:
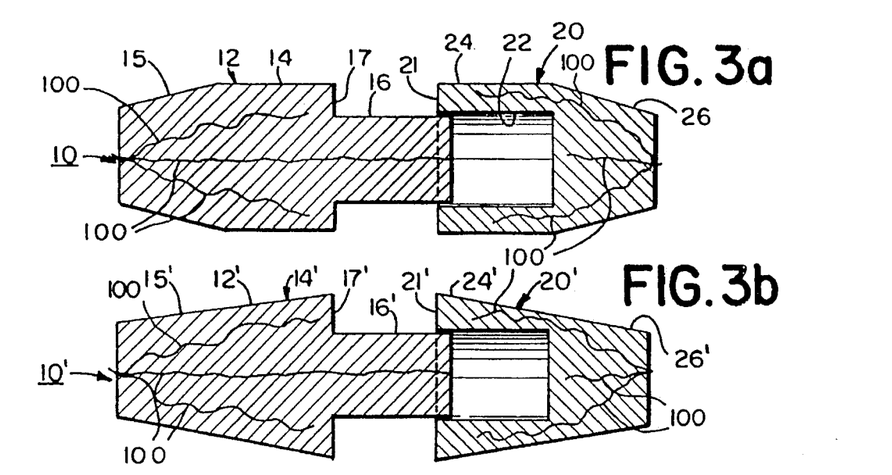
FIG. 3a is a cross-sectional view along a longitudinal axis of the embodiment of a dissolvable stent for mammalian anastomoses according to the present invention illustrated in FIG. 2.
FIG. 3b is a cross-sectional view along a longitudinal axis of another embodiment of a dissolvable stent according to the present invention.
Figure 4:
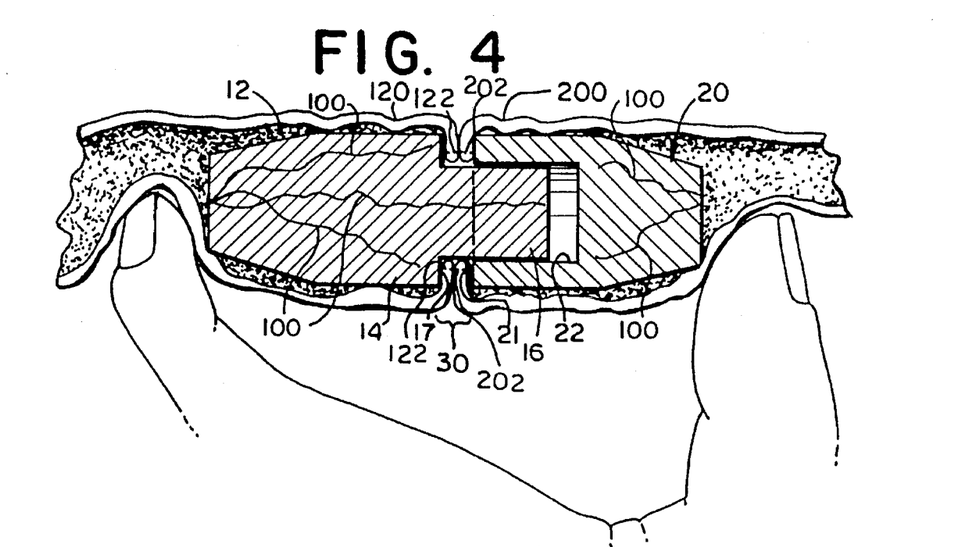
FIG. 4 is a partial cross-sectional view along a longitudinal axis showing a dissolvable stent inserted into two vessel stumps during one embodiment of a surgical anastomosis procedure.
Figure 5:
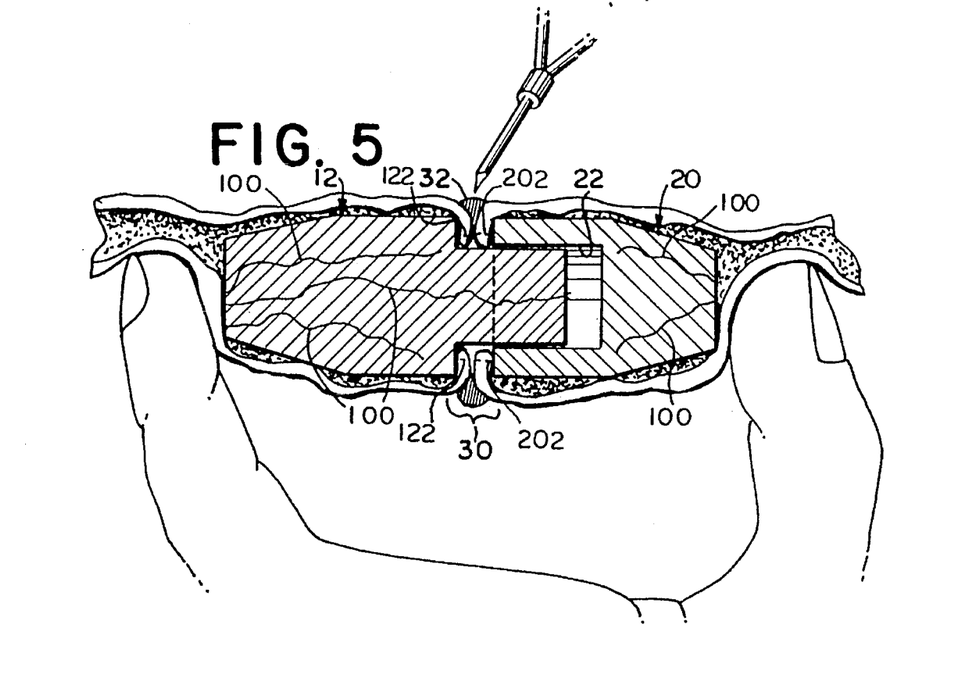
FIG. 5 is a partial cross-sectional view along a longitudinal axis showing the anastomosis procedure of FIG. 4 at a later stage.

Referring to the drawings, wherein like numerals indicate like elements throughout the several views, there is shown in FIGS. 2 and 3a a dissolvable stent 10 for mammalian anastomoses in accordance with the present invention. The stent 10 comprises at least a first or male member 12 for receiving a first vessel stump 120 and preferably a second or female member 20 for receiving a second vessel stump 200. The first member 12 has a first end 14 and preferably has an integrally formed engaging means or second end 16 engageable within a cavity 22 formed in the second member 20, preferably by slidable insertion along the central longitudinal axis of the members as seen in FIGS. 3a, 4 and 5.

Figure 3C:
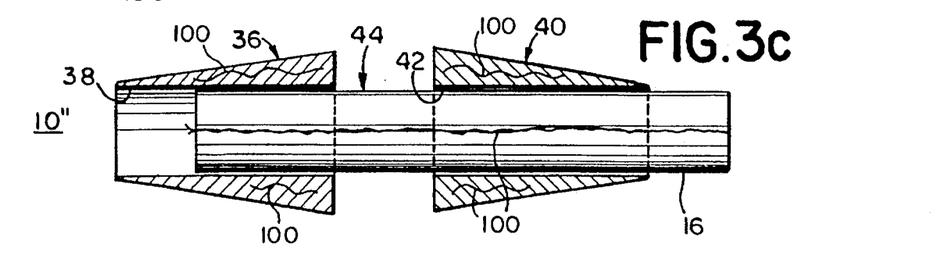
FIG. 3c is a partial cross-sectional view along a longitudinal axis of still another embodiment of a dissolvable stent for mammalian anastomoses according to the present invention.

Other embodiments of basic versions of a dissolvable stent according to the present invention are illustrated as stents 10' and 10" in FIGS. 3b and 3c, respectively. Because stent 10' is very similar to the construction of stent 10, the numerals representing components of FIG. 3b are primed compared to those components of FIGS. 2 and 3a having similar functions. Still other embodiments according to the present invention illustrated in FIGS. 6 through 15, comprise a dissolvable stent and a removable stent insertion tool or anastomosis apparatus 50, 50', 50" and 50'".

The stents according to the present invention are constructed of a biocompatible, non-toxic material which substantially completely dissolves in mammalian bodily fluids. As used herein, the term "substantially completely dissolves" and equivalent terms mean that the stent material, except for reinforcing means in certain situations discussed below, dissolves to the extent that any remnant would not be harmful when used in the mammal's body according to the present invention. The stent serves the purpose of an intraluminal support for vessel anastomoses and, in such capacity, should be constructed of a material capable of maintaining its structural integrity and the integrity and patency of the vessel in which it is inserted for a period of time necessary to complete the surgical anastomosis procedure.

It is presently preferred to provide the stent with reinforcing means 100, which are biocompatible, and are preferably, but not necessarily in all situations, formed of dissolvable or absorbable materials. The reinforcing means need not always be dissolvable. For example, where the stent is used in anastomosis procedures in the gastrointestinal tract, non-dissolvable, biocompatible reinforcing means, such as non-absorbable sutures, would be eliminated eventually with feces. The reinforcing means 100 should extend at least partially through the stent body and preferably generally axially throughout at least one portion of each member of the stent. Presently preferred materials suitable as reinforcing means include a plurality of absorbable sutures, although other biocompatible thread-like materials, string-like materials, fibers or other materials suitable for reinforcing the stents of the present invention may be used.

It is preferred to have the stent dissolve over a period of time sufficient to avoid problems or complications associated with vessel blockage caused when the stent is inserted. Preferably, the stent is constructed of a material which substantially completely dissolves over a period of time to be determined by the particular use and environment of the stent, which may vary from about 1 to about 2 minutes for very small vascular stents to about 10 minutes to about 10 hours for large vessels. The larger times are for stents used for larger vessels, such as the intestine; dissolving times would be substantially shorter for smaller lumen vessels. Preferably, the stent dissolves in about 10 minutes to about 1 hour for vessels of average size. One presently preferred biocompatible, non-toxic material of which the dissolvable stent is constructed comprises a crystallized saccharide, although one skilled in the art will appreciate that other dissolvable, biocompatible, non-toxic materials may be used in accordance with the present invention. The presently preferred saccharide comprises sucrose, although other saccharides may be used in accordance with the present invention.

Saccharides, and sucrose in particular, are easy to work with and are relatively inexpensive. It may be desired, however, to include additional binders, such as gelatin and cellulose, for example, and/or fillers, such as sorbitol and dicalcium phosphate, for example, and/or excipients, such as silica, stearic acid, citric acid and magnesium stearate, for example, to achieve the desired hardness and dissolving time.

The dissolvable stent 10 according to the present invention is manufactured by dissolving the biocompatible, non-toxic solid material in a biocompatible, non-toxic liquid at a temperature sufficient to form a liquid solution. For example, where the non-toxic solid material comprises sucrose, the non-toxic liquid used may be water. Depending on the concentration of the solution desired, the solid and liquid mixture may be heated to allow the solid material to dissolve.

Sutures or other biocompatible reinforcing means 100 could be supported within the molds at desired locations prior to pouring the solution into the mold. Alternatively, the reinforcing means could be inserted into the solution as it begins to solidify but before the material fully solidifies.

The liquid solution is then poured into molds (not shown) having shapes complementary to the member components of the stent 10 to form the various member components of the stent 10. One skilled in the art will readily appreciate in view of this disclosure that many different molds may be used in the manufacture of a dissolvable stent 10 in accordance with the present invention, such as metal (aluminum, e.g.), plastic and other materials, depending on the temperature of the solution to be poured into the mold and the intricacy of the shape desired, among other factors.

The liquid solution is then allowed to solidify in the molds to form the members comprising the stent 10 according to the present invention. The solidified members are then removed from the mold and are ready for use in anastomosis procedures or may be stored in appropriate storage facilities for future use.

The overall shape and dimensions of the stent 10 according to the present invention will vary depending on the intended anastomosis use, such as end-to-end, isoperistaltic, side-to-side, antiperistaltic, side-to-end and end-to-side anastomoses. The dimensions of the stent 10 will also vary depending on the size of the vessel or vessels undergoing anastomosis, such as the intestine, stomach, gallbladder and blood vessels, among others. The reinforcing means should be absorbable or dissolvable where the stents of the present invention are intended for use with blood vessels or other vessels where there is a risk of thrombosis or other adverse effects from using non-absorbable or non-dissolvable reinforcing means.

For illustrative purposes, the various embodiments of the stent as illustrated in the drawings are intended for use in end-to-end and end-to-side anastomosis procedures (esophagoileostomy, cholecystojejunostomy, colocolostomy, ileoileostomy, ileocolostomy, etc). Preferably, the male member 12 has a first end 14 having a first circumference and an integrally formed second, projecting end 16 having a second circumference smaller than the first circumference. Preferably also, the female member 20 has a first end 24 having an outer circumference substantially the same as the first circumference of the first end 14 of the male member 12 and an inner circumference 22 that at least partially receives the second end 16 of the male member 12.

The first end 14 of the male member 12 preferably, but not necessarily, has a tapered end portion 15. The female member 20 has a second end 26 which preferably, but not necessarily, is also tapered. The tapered portions or ends of the male and female members aid in the insertion of the male and female members into the respective vessel stumps. If desired, as illustrated in the embodiment of FIG. 3b, the male and female members 12' and 20', respectively, have a truncated tapered shape extending from their first ends 14' and 24', respectively, to their tapered end portion 15' and second end 26', respectively. In addition, the male member 12 and female member 20 are generally circular in cross-section to accommodate and adapt to the general shape of the lumen of the vessel undergoing anastomosis.

It is preferred in accordance with the present invention that the female member 20 receive the male member 12 in a generally friction free manner so that the male member 12 is slidingly removable from the cavity 22 of the female member 20. Thus, as discussed below in further detail, when compressive force on the two stent members is released, the stent members may separate relatively freely, thereby reducing the compressive and circumferential forces at the anastomosis site. The circumference of the second end 16 of the male member 12 is slightly less than the inner circumference of the cavity 22 of the female member to allow the second end 16 to fit and move freely within the female member 20.

The stent 10 according to the present invention as illustrated in FIG. 3c is constructed to have two hollow female members 36 and 42 having cavities or bores 38 and 40, respectively, which slidingly engage a central core 44 functioning as the second projecting end 16 or 16' of male members 12 and 12' of FIGS. 3a and 3b, respectively. The central core 44 may be attached to either of the hollow female members 36, 42 by extending a reinforcing member 100 in the central core, either as a single or multifiber unit, out the distal end of the core and into one hollow female member. This prevents the core member from prematurely sliding out from the hollow female member either during or after the anastomosis, assuming the therapeutic advisability of retaining the core member in the female members during a particular anastomosis procedure. One skilled in the art will appreciate that a stent according to the present invention may be constructed to have other configurations depending on the particular anastomosis procedure desired to be performed using the stent 10.

Especially in intestinal anastomoses, there must be complete serosa to serosa (outer vessel surface to outer vessel surface) contact to have an effective surgical procedure. Accordingly, the dissolvable stent 10 of the present invention is configured to allow for introflection of the edges of the vessel stumps during surgical anastomosis procedures. Thus, as illustrated in FIG. 4, the circumference of the second, projecting end 16 of the male member 12 is sufficiently smaller than the circumference of the first end 14 of the first or male member 12 and the outer circumference of the second or female member 20 to allow annular introflection of vessel stump edges at a position between the male and female members. The introflected edges of the vessel stumps are temporarily clamped between the face 17 of the male member 12 and the adjacent face 21 of the female member 20.

The difference between the circumferences of the first and second ends may be expressed as a ratio of the circumference of the first end 14 of the first or male member 12 (or first member 36) to the circumference of the second, projecting end 16 of the male member 12 (or core 44) of the stent 10 and is sufficiently large to allow for introflection of the vessel stump edges. It is preferred that the ratio of the circumference of the first end 14 of the male member 12 to the circumference of the second end 16 of the male member 12 is about 4.0:1 to about 1.25:1. A ratio of about 2:1 is presently used most frequently. One skilled in the art will readily appreciate that the ratio between the first and second circumferences of the ends 14, 16 of the male member 12 may be greater or less depending on the type, size, and wall thickness of the vessel into which the stent 10 is to be inserted.

Figure 1:
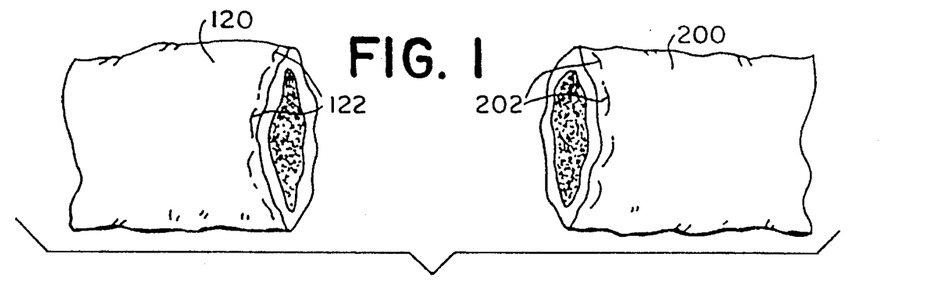
FIG. 1 is a side elevational view of two vessel stumps having purse-string sutures therein.

Further in accordance with the present invention, surgical mammalian vessel anastomosis connecting a first vessel stump 120 and a second vessel stump 200 as illustrated in FIGS. 1, 4 and 5, comprises circumferentially inserting purse-string sutures (122, 202) into the first and second vessel stumps (120, 200), respectively, to assist introflection of the vessel stump edges during the procedure. Conventional suturing techniques may be used, such as those disclosed by T. G. Hardy et al., "Initial Clinical Experience With a Biofragmentable Ring for Sutureless Bowel Anastomosis," *Dis. Col. & Rect.*, 30:55 at p. 58 with the exception that the purse-string sutures are usually not tied and eventually withdrawn before completing the anastomosis.

Once the vessel stumps have been sutured, the first end 14 of the male member 12 is inserted into the opening of the first vessel stump 120 and the second end 26 of the female member 20 is inserted into the opening of the second vessel stump 200 as illustrated in FIG. 2. The second end 16 of the male member 12 is then partially inserted into the cavity 22 at the first end 24 of the female member 20. The purse-string sutures (122, 202) are then tightened to annularly introflect the edges of the first and second vessel stumps (120, 200) onto the second end 16 of the male member 12 of the stent 10. The sutures are not usually tied, but are held tightly to keep the stump margins in place on the core 16.

With the male and female members of the stent 10 axially aligned, the second end 16 of the male member 12 is inserted farther into the cavity 22 of the female member 20 to cause the annularly introflected edges of the first and second vessel stumps to engage, forming a substantially annular engagement region. This may be done by applying an axial force on the ends of the stent members with surgical apparatus as illustrated in FIGS. 6 through 11 or the surgeon's hand as illustrated in FIGS. 4 and 5 and applying a compressive force sufficient to hold the introflected edges in substantially complete engagement with the aid of the tightened purse-string sutures. The stent members are brought together with a clamping force sufficient to maintain the edges of the stumps in annular engagement region 30 between the faces 17 and 21 of the male and female members, respectively.

While maintaining the annular engagement region 30 under compressive forces, a biocompatible sealant 32 is preferably applied to the external surfaces of the first and second vessel stumps (120, 200) in an amount sufficient to substantially entirely cover the engagement region as illustrated in FIG. 5. It is preferred that the purse-string sutures (122, 202) are then removed from the vessel stumps (120, 200) after the sealant cures sufficiently while the introflected ends of the vessel stumps are clamped together, although it is possible to remove the purse-string sutures (122, 202) prior to applying the biocompatible sealant 32. With the presently preferred fibrin glue (containing 4 international units of thrombin), there is sufficient curing after about 6 minutes. It will be appreciated by one skilled in the art that, where the purse-string sutures (122, 202) are removed (either before or after the sealant 32 is applied), the biocompatible sealant 32 is applied in a manner sufficient to cover any holes in the vessel stumps left after removing the sutures.

Once the sealant 32 has solidified or cured sufficiently to maintain adhesion at the annular engagement region 30, the compressive force on the stent members may be released and the stent 10 may, if desired, be moved away from the anastomosis site or even removed, where, for example, the stent was applied using an insertion device (discussed below).

The biocompatible sealant may comprise any non-toxic sealant which can effectively hold and seal living tissue in the mammalian body. One example of a presently preferred biocompatible sealant is a fibrin sealant comprising fibrinogen and thrombin commercially available as the TISSUCOL™ sealant manufactured by Immuno AG, Vienna, Austria. Another example of a suitable biocompatible sealant is described by T. Kamiji et al., "Microvascular Anastomosis Using Polyethylene Glycol 4000 and Fibrin Glue," *Brit. J.*

*Plas. Surg.*, 42:54–58 (1989). In view of the present disclosure, one skilled in the art will appreciate that other biocompatible sealants presently available and those which may be developed may also be used to seal the vessel stumps.

Where a stent is desired for use in relatively harder to reach areas, such as the lower rectum and the esophagus, an anastomosis apparatus (50, 50', 50" or 50''') according to the present invention is preferably used. Although the same anastomosis apparatus can be utilized for end-to-side anastomoses, for example, the apparatus is discussed below and illustrated in the drawings in end-to-end anastosmoses. Referring to FIGS. 6 through 8 and 9 through 11, an anastomosis apparatus (50, 50') comprises a housing 60 having at the rear end a handle 62. A stent member 12" and a stent placement member 52 are received in the front end of the housing. The stent member 12" preferably comprises essentially the same features as the male member 12 of the stent 10 described above and preferably further comprises a connecting member 114 secured thereto. Preferably also, the second end 16" of the stent member 12" is longer than the second end 16 of the male member 12 so that it is stable when partially extended from the stent placement member 52 and so that it can accommodate both vessel stumps when released from the stent placement member 52.

Figure 6:
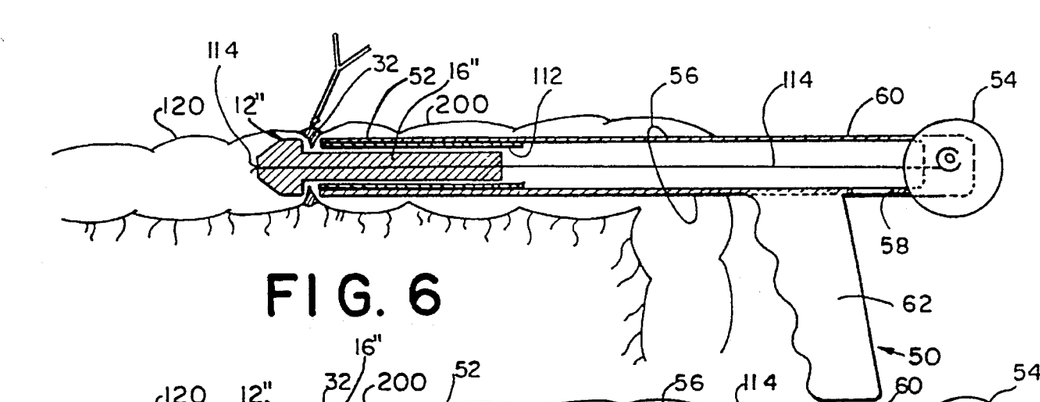
FIGS. 6 through 8 are schematic diagrams illustrating a second embodiment of a surgical anastomosis procedure using an anastomosis apparatus according to the present invention.
Figures 7, 8:
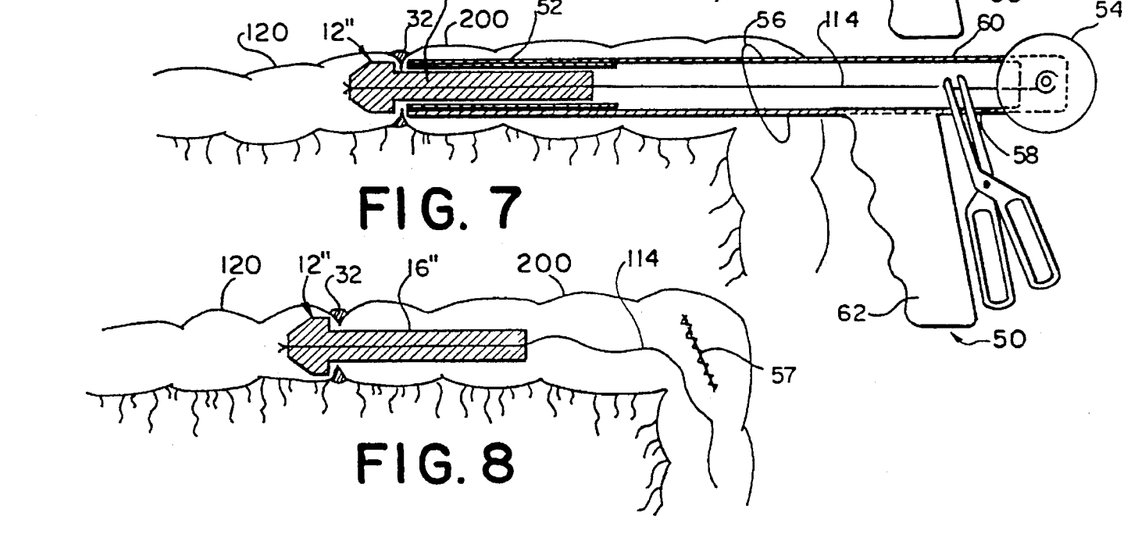

The stent member 12" and stent placement member 52 at the end of the anastomosis apparatus 50 opposite the handle 62 are inserted into an access hole 56 made surgically in the vessel 200 as schematically illustrated in FIGS. 6 and 7. The access hole could also be a natural opening, such as the mouth or anus, where possible and appropriate.

In the embodiments of FIGS. 6–11, the connecting member 114 preferably comprises a biocompatible, absorbable or dissolvable cord, such as absorbable suture thread or string for example, and may be secured to the stent member 12" preferably by being embedded at least partially within the stent member, where the connecting member may also serve as a reinforcing means where desired.

The anastomosis apparatus embodiments 50" and 50''' illustrated in FIGS. 12–15 and described in detail below, use rigid connecting members 114', 114", but generally are used in the same manner as described in the following anastomosis procedure according to the present invention using the embodiments of FIGS. 6–11.

The stent placement member 52 of the present invention may be formed of plastic, metal or other surgically acceptable materials and may be either rigid or flexible. The stent placement member 52 has an outer circumference preferably substantially the same as the first circumference of the stent member and an inner circumference (112, 112") for at least partially receiving the second end 16" of the stent member 12". It is presently preferred in accordance with this invention that the stent placement member 52 receive the stent member 12" in a generally friction free manner so that the stent member is sidingly removable from the stent placement member.

The stent placement apparatus 50, 50' further comprises a compression retaining means for applying and holding a compressive force on the clamping member. The compression retaining means may be a simple tube through which the connecting means 114 in the form of a thread-like material extends, held by a friction-fit plug. Alternatively, and preferably, the compression retaining means includes a mechanical member, such as a reel member 54 attached to the stent placement. The reel member 54 is functionally attached to the connecting member 114, preferably in a manner similar to many types of fishing line and reels, so that the reel member 54 may be rotated to pull the connecting member 114 onto the reel (or released from the reel), thus forcibly pulling the stent member 12" toward and at least partially within the receiving portion of stent placement member 52. The reel member 54 may also be used in conjunction with the connecting member 114 to apply and maintain compressive force on introflected vessel stump ends during anastomosis procedures. The reel member 54 may be provided with any of several known types of a friction or ratchet mechanism and handle or other driving means, such as a handle and worm gear assembly (not shown) of a type known in the fishing reel art, for example, to assist rotating and locking the reel member where desired. When the stent member 12" is pulled into the stent placement member 52, the stent member and the receiving portion of the stent placement member are preferably substantially axially aligned as shown in FIGS. 6, 7, 9 and 10.

Figure 9:
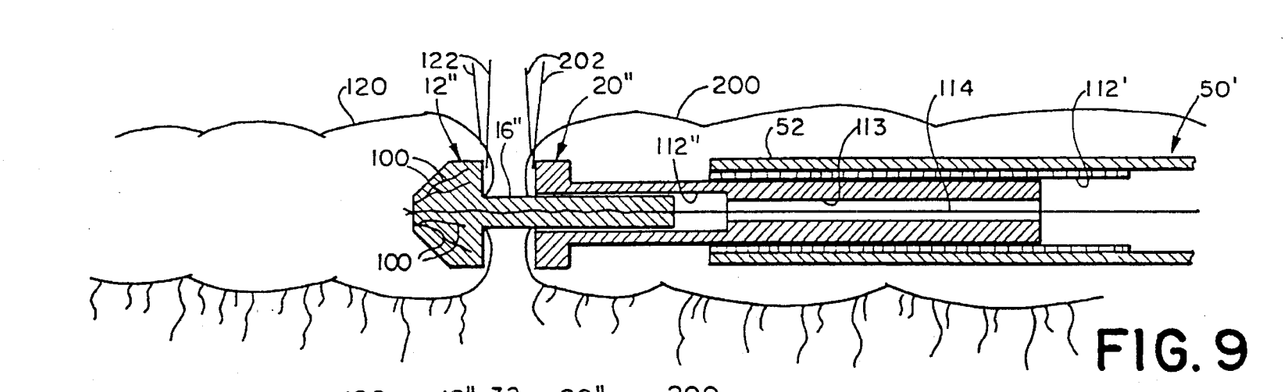
FIGS. 9 through 11 are schematic diagrams illustrating a third embodiment of a surgical anastomosis procedure using another anastomosis apparatus in accordance with the present invention.
Figure 10:
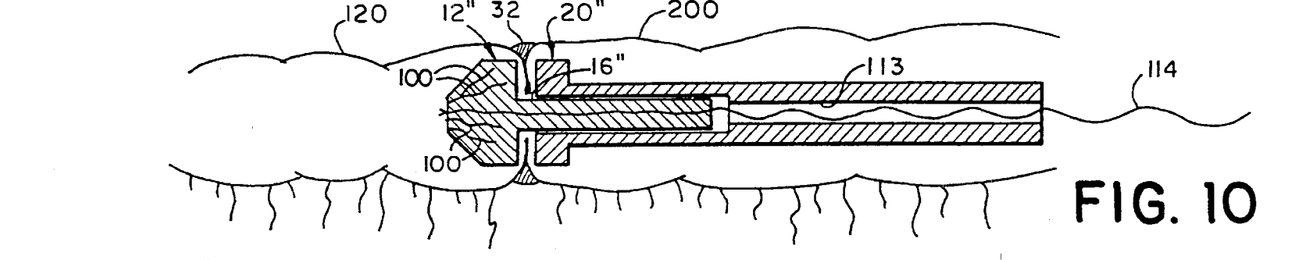
Figure 11:
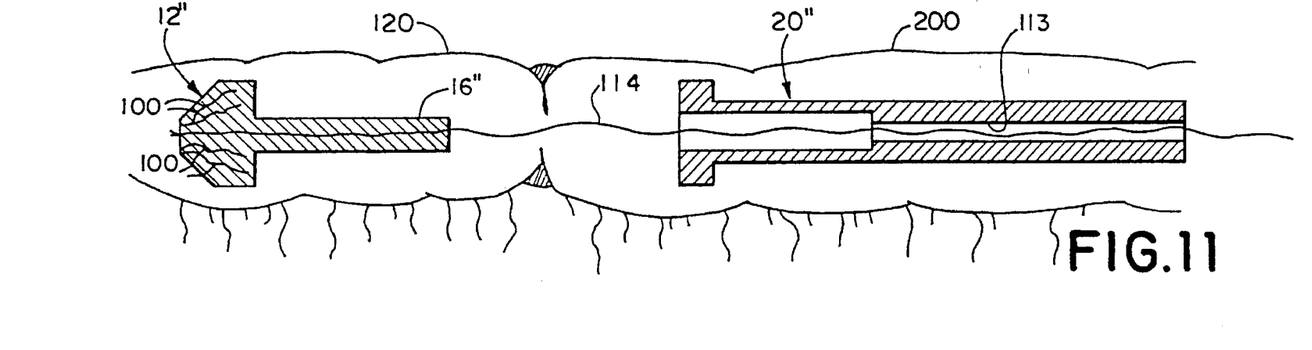

The stent placement member 52 may alternatively be provided with stent insert 20" as shown in FIGS. 9 through 11 where it is desired to have some internal support for the vessel stump after the stent placement member is removed. The stent insert 20" preferably comprises essentially the same features as the female member 20 of the stent 10 described above, with or without reinforcing means, but preferably with reinforcing means, and should be formed so as to fit at least partially through the stent placement member 52, preferably without friction, and allow the connecting means 114 to be functionally connected to the reel member 54.

Using the anastomosis apparatus (50, 50') of the present invention, surgical mammalian vessel anastomosis connecting a first vessel stump 120 to a second vessel stump 200 as illustrated in FIGS. 6 through 11 comprises circumferentially inserting purse-string sutures (122, 202) into the first and second vessel stumps (120, 200), respectively, to assist introflection of the vessel stump edges during the procedure in a manner described above. Once the vessel stumps have been sutured, the stent member 12" and the removable stent placement member 52 are inserted through an opening 56 through the second vessel stump or through a body orifice such as the mouth or anus. Where the mammalian vessel is an intestine, the opening 56 may be made using conventional enterotomy procedures, for example, preferably about 15 to about 20 cm above or below the anastomosis site, depending on the size of the anastomosis apparatus (50, 50') and the size of the vessel.

The stent member 12" and stent placement member 52 are inserted through the second vessel stump or orifice until the stent member 12" extends at least partially through the generally annular opening of the second vessel stump. At this point, the stent member 12" and stent placement member 52 are inserted farther into the opening 56 so that the first end of the stent member 12" is inserted into the generally annular opening of the first vessel stump 120 as shown generally in FIGS. 6, 7, 9 and 10. Once the stent member 12" is positioned, the purse-string sutures are tightened as discussed above to annularly introflect the edges of the first and second vessel stumps toward the reduced diameter of the second end 16" of the stent member 12".

The connecting member 114 is then reeled farther onto the reel member 54 to further pull the stent member 12" through the stent placement member 52 to cause the annularly introflected edge of the first vessel stump to engage the annularly introflected edge of the second vessel stump to engage, forming a substantially annular engagement region. The connecting member 114 is reeled onto the reel member 54 with and until an axial force on the stent member 12" and stent placement member 52 is sufficient to hold the introflected edges in substantially complete engagement and retain the edges of the stump in the annular engagement region, aided by the tightened purse-string sutures.

While retaining the annular engagement region under compressive forces using the connecting member 114 and reel member 54, a biocompatible sealant 32 is preferably applied to the external surfaces of the first and second vessel stumps (120, 200) as discussed above with reference to FIG. 5. It is preferred that the purse-string sutures (122, 202) are then removed from the vessel stumps (120, 200) while the introflected ends of the vessel stumps are clamped together, although the sutures may be removed prior to applying the biocompatible sealant 32. As discussed above, additional biocompatible sealant may then be applied in a manner sufficient to cover any holes in the vessel stumps left after removing the purse-string sutures.

Once the sealant 32 is solidified or cured sufficiently to maintain adhesion at the annular engagement region, the compressive force on the stent members or on the stent member and the stent placement member may be released by unwinding the connecting member 114 from the reel member 54, and preferably then cutting the connecting member 114 as illustrated in FIG. 7 or otherwise releasing the connecting member from the reel member 54. Cutting of the connecting member can be facilitated by providing an access opening 58 in the stent placement member 52. The stent placement member is then withdrawn from its access hole 56 (which is closed manually or mechanically as shown by schematically illustrated sutures 57) or withdrawn from the anus in a low rectum transanal approach, or from the mouth in a transoral approach for the upper esophagus.

The procedures described above for mammalian vessel anastomosis using the anastomosis apparatus of the present invention is substantially the same whether or not a stent insert 20" is used, as shown in FIGS. 9–11, or is not used, as shown in FIGS. 6–8, 12 and 13.

The embodiments of the anastomosis apparatus according to the present invention illustrated in FIGS. 12 through 15 are directed to equipment in which a more rigid elongated member acts as the connecting member between the apparatus and the stent member. In some instances, it is desirable to have more control over the placement of the stent member by making it easier to maneuver the stent member in various positions within the first and second vessel stumps. In general, when using the apparatus of FIGS. 12 through 15, the anastomatis procedures are substantially as described above with respect to the embodiments illustrated in FIGS. 6 through 11. Accordingly, the following descriptions of the embodiments of FIGS. 12 through 15 will only provide details of the differences in the apparatus and their use compared to those set forth above.

Figure 12:
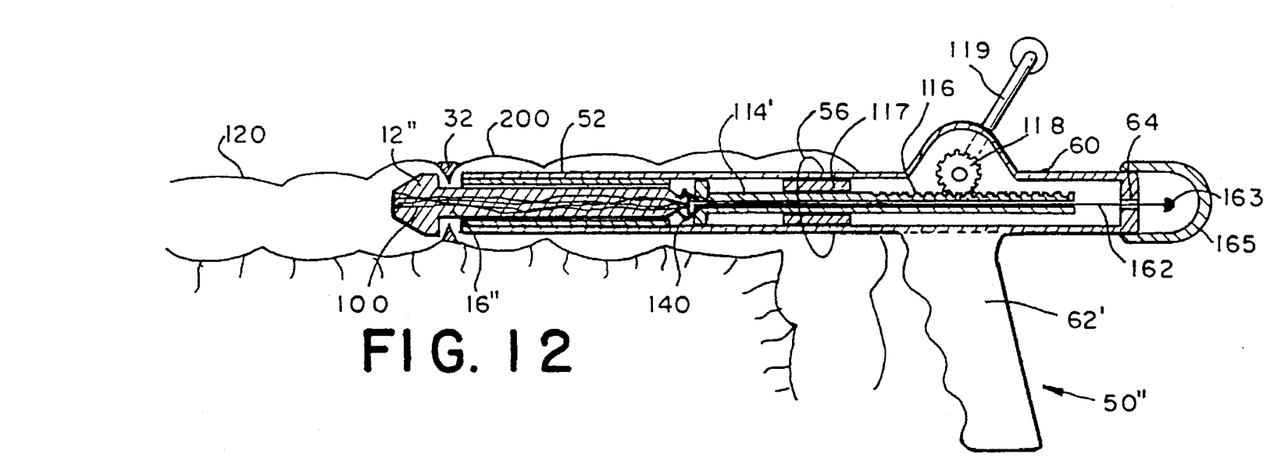
FIG. 12 schematically illustrates the use of another alternative embodiment of an anastomosis apparatus for performing a surgical anastomosis procedure in accordance with the present invention.
Figure 14:
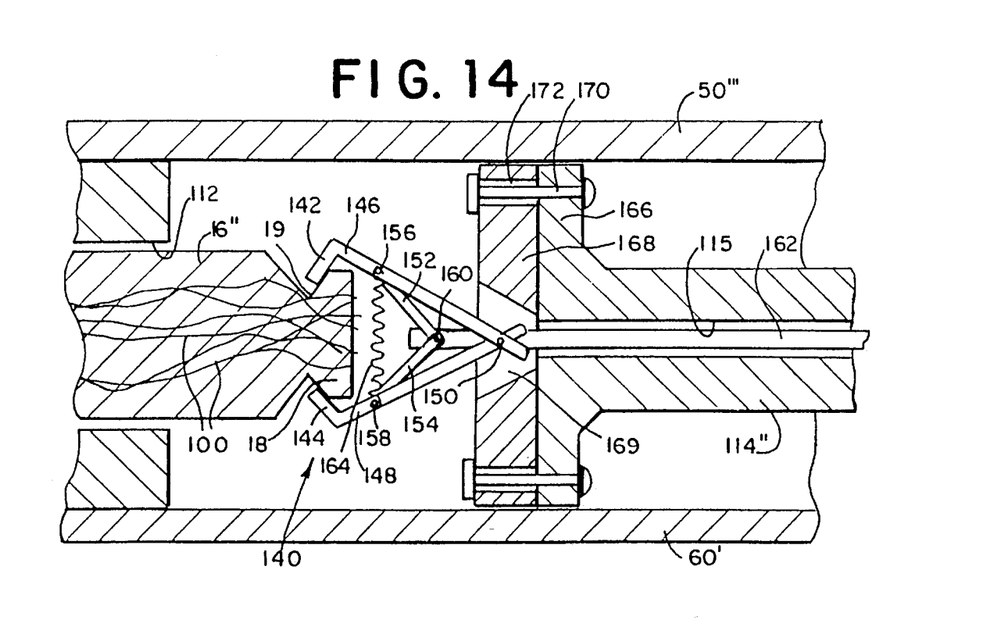
FIG. 14 illustrates, in enlarged detail, portions of the anastomosis apparatus illustrated in FIGS. 12 and 13, and is directed to a gripping means holding the end of the stent member.
Figure 15:
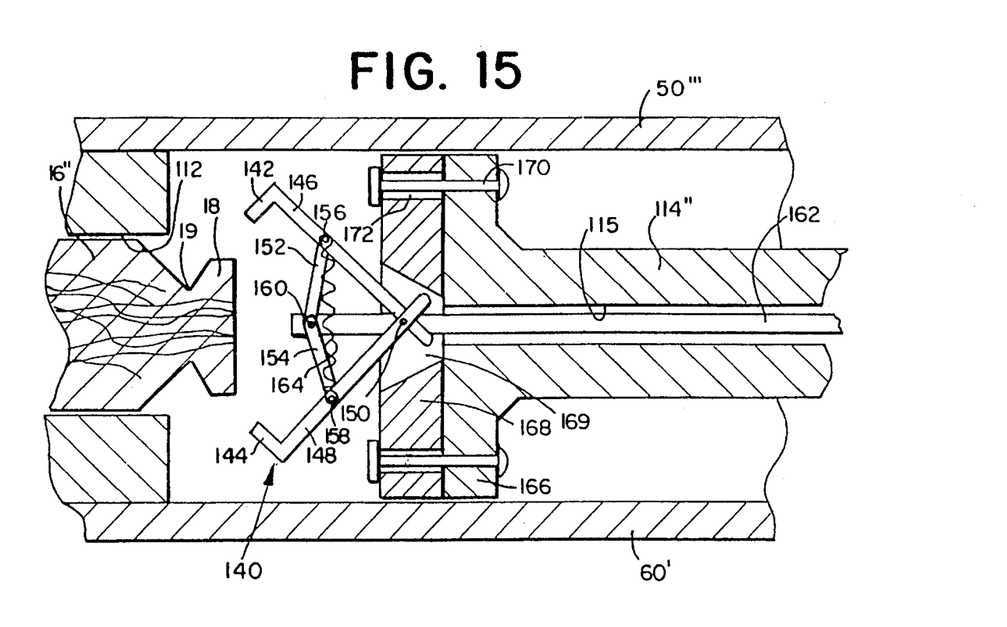
FIG. 15 shows the gripping means of FIG. 14 where the gripping means is released from the end of the stent member.

FIG. 12 illustrates schematically the use of an anastomosis apparatus 50". Apparatus 50" includes a housing 60, a handle 62' and a stent placement member 52 at the end of the housing opposite the handle. The stent member 12" is inserted into the stent placement member 52 where it is held in place by a generally rigid elongated connecting member 114' by a gripping means 140 as described below with reference to a particular embodiment as illustrated in FIGS. 14 and 15.

In use, apparatus 50" containing the stent member 12" is inserted into a vessel 200 through an access hole 56. The apparatus 50" and stent member 12" are manipulated until the stent member 12" extends from the stent placement member 52 into the vessel stump 120 with the second end 16" of the stent member being retained within the stent placement member 52 which is located in the vessel stump 200. The alignment of the stent member 12" is aided by the ability to extend the second end 16" axially within the stent placement member 52 by use of a rack and pinion arrangement formed on the rigid connecting member 114'.

The rigid connecting member 114' is supported within the housing 60 by a hollow support member 117. A portion of the connecting member 114', distal to the area of connection between the connecting means 114' and the second end 16" of the stent member 12", is provided with notches 116 in the form of an elongated notched rack. A pinion gear 118 has teeth corresponding to the notches 116 formed in the rack portion on the connecting member 114'. The pinion gear 118 is rotated by means of a handle 119 extending from the housing 60.

In the orientation illustrated in FIG. 12, when the handle is rotated clockwise, the second end 16" of the stent member is extended outwardly from the stent placement member 52. When the handle is rotated counterclockwise, conversely, the stent member second end 16" is retracted within the stent placement member 52. As explained below with respect to FIGS. 14 and 15, the gripping means 140 may be actuated by the movement of a pushrod 162 extending axially within the connecting member 114' and extending out of the housing 60 through an axial opening 64. A pushrod stop button 163 is formed on the end of the pushrod 162 which extends out of the housing 60. A removable transparent or translucent cap 165 through which the stop button 163 can be seen, fits over the end of the push rod stop button to avoid accidentally actuating the push rod 162. The cap 165 may be screwed on the end of the housing 60 (or handle 162 in FIG. 13) or may be retained on the housing by a friction fit, among various other means of removable connecting the cap to the housing or handle.

Once the stent member 12" and stent placement member 52 are in the desired locations within vessel stumps 120 and 200, respectively, purse-string sutures may be provided in the ends of the vessel stumps as described above with respect to FIGS. 6 through 11 to annularly introflect the edges of the first and second vessel stumps 120, 200 onto the second end 16" of the stent member 12". A relative compression force between the stent member 12" and the stent placement member 52 is maintained by moving the handle 119 counterclockwise so that the second end 16" is retracted within the stent placement member 52. This causes the rear surface of the head of the stent member 12" to clamp the introflected vessel stumps between the stent member and the stent placement member 52. A biocompatible sealant 32 is then applied as described above, the purse-string sutures are removed and additional sealant 32 may be applied to any holes remaining after removing the purse-string sutures.

Once the sealant 32 is cured sufficiently to maintain adhesion at the annular engagement region between the two vessel stumps, the compressive force between the stent member 12" and the stent placement member 52 may be released by rotating the handle 119 clockwise and releasing the gripping means 140 from the second end 16" as described below. The stent placement member 52 may be removed from the vessel 200 by withdrawing the apparatus 50" from the access opening 56 which may be closed by suturing, clamping, stapling or in any other suitable manner.

Figure 13:
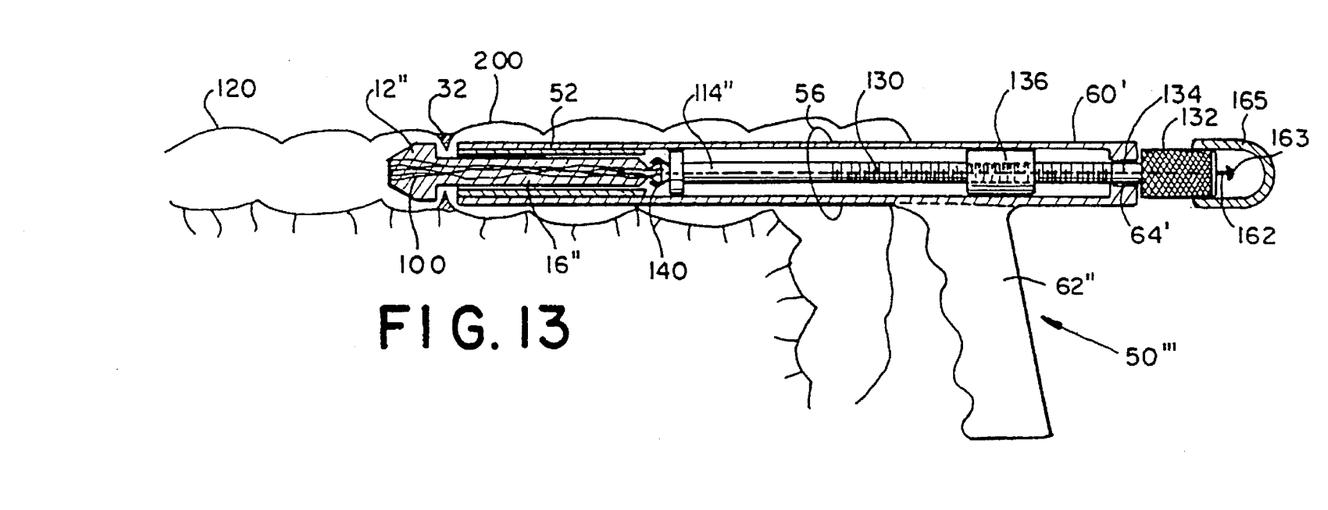
FIG. 13 schematically illustrates the use of yet another alternative embodiment of an anastomosis apparatus for performing a surgical anastomosis procedure in accordance with the present invention.

FIG. 13 illustrates another embodiment of an anastomosis apparatus 50''' which may be used as just described with respect to FIG. 12 except in the following respects. Apparatus 50''' includes a generally rigid connecting member 114" which has threads 130 along a portion of its length. A handle 132, such as a knurled handle, is attached to the distal end of the connecting member 114" so as to extend from the housing 60', preferably beyond the handle 62". The distal portion of the connecting member 114" may have a bushing 134 within axial bore 64' of the housing 60'.

The connecting member 114" preferably is hollow as illustrated in FIG. 13 so that a pusher rod 162 may extend through an axial bore within the connecting member to activate the gripping means 140. A pushrod stop button 163 extends beyond the end of the knurled handle 132.

In the embodiment of FIG. 13, the axial alignment of the stent member second end 16" is adjusted by turning the knurled handle 132. The threaded portion of the connecting member 114" is supported within the housing 60' by an internally threaded bushing 136 in which the internal threads of the bushing 136 match the external threads 130 formed on the connecting member 114". Thus, when the knurled handle 132 is turned in one direction, clockwise, the stent member 12" may extend away from the stent placement member 52. When the knurled handle is turned in the opposite direction, the second end 16" of the stent member 12" is retracted axially within the stent placement member 52. In this way, a sufficient compressive force may be maintained for a sufficient time between the stent member 12" and the stent placement member 52.

If desired, the connecting member 114" of the embodiment illustrated in FIG. 13 need not be rotatable. This can be accomplished by having an internally threaded bushing or nut rotatable in a fixed axial position with respect to the housing 60', so that when the bushing or nut is rotated, the threaded portion of the connecting member 114" will move axially within the bushing or nut, thus making the entire connecting member reciprocate within the housing. Of course, in this arrangement, the connecting member 114" must be prevented from rotating with the rotating bushing or nut. A key and slot arrangement would be one way of preventing such rotation, for example.

When the anastomosis procedure is completed as described above, the compressive force is released by turning the knurled handle in the appropriate direction, removing the cap 165 and pushing the pushrod 162 or the pushrod stop button 163 to release the end of the stent member from the gripping means 140. The apparatus 50''' is then removed from the access hole 56 which may be closed as described above.

There may be calibration marks, placed on or formed in the housing 60, connecting members 114' or 114", push rod 162 or other components of the insertion tools 50" and 50'''. The calibration marks would allow an accurate determination of how far the stent member second end 16" is extended from or retracted within the stent placement member 52.

The details of the gripping means 140 are illustrated in FIGS. 14 and 15. FIG. 14 illustrates the gripping means in the closed position, while FIG. 15 illustrates the gripping means in the open position. Other types of gripping means may be used other than the embodiment illustrated, as long as the second end 16" of the stent member 12" may be adequately gripped and released as desired. The second end 16" should be well reinforced with reinforcing means 100 throughout its length and cross sectional area to provide a secure gripping area for the gripping means.

FIGS. 14 and 15 illustrate a gripping means 140 which is particularly suited for a connecting member 114" which may be rotated by turning a knurled handle 132 as described above with respect to FIG. 13. The same structure could also be used with respect to the connecting member 114' of FIG. 12, even though the connecting member 114' is not intended to be rotated axially. The stent member may be formed such that the second end 16" may have a terminal portion 18 with an intermediate notched portion 19 as illustrated. Preferably, the stent member is so formed during the molding process, although the terminal and notched portions 18 and 19 could be formed by machining a stent member after it is molded with the second end 16" having a uniform diameter.

The gripping means 140 includes a upper jaw 142 and a lower jaw 144 which engages the terminal portion 18 of the second end 16" of the stent member. The upper jaw 142 is connected to an upper yoke 146 which may be in the form of a pair of opposed arms, only one of which is shown for the purpose of clarity. The lower jaw 144 may likewise be connected to a lower yoke 148 in the form of a pair of opposed arms. The arms of the upper and lower yokes 146 and 148, respectively, are attached by pivot pins 150, only one of which is shown. The opposed arms forming the respective yokes 146 and 148 may be connected by transverse sections extending below and above the pushrod 162 as shown in FIGS. 14 and 15.

The pushrod 162 passes through the connecting member 114" by extending through an axial bore 115 in the connecting member 114". The opposite end of the pushrod near the rear of the housing 60, 60' may be selectively clamped or retained in a desired position with respect to the connecting member 114', 114" or with respect to the housing 60, 60', by any suitable means well known to those skilled in the art, such as cam locks, lock nuts, set screws, etc. Two pairs of actuating arms, a pair of upper actuating arms 152 (only one of which is shown) and a pair of lower actuating arms 154 (only one of which is shown) are connected by pivot pins 156 and 158, respectively, to the respective arms of the upper yoke 146 and lower yoke 148. A pivot pin 160 connects the two pair of upper actuating arms 152 and lower actuating arms 154 and passes through the pushrod 162. Extension springs 164 extending between pivot pins 156 and 158 normally hold the upper and lower jaws 142 and 144 in a closed, gripping condition as illustrated in FIG. 14. To open the gripping means 140, releasing the jaws 142 and 144 from the terminal end 18 of the second end 16" of the stent member, one merely releases the pushrod clamping means and pushes the pushrod 162 with sufficient force to overcome the spring bias created by the springs 164 until the jaws 142 and 144 are opened to release their grip on the terminal portion 18 of the second end 16" of the stent member.

The end of the rotatable connecting member 114" is constructed to allow for the rotation of the connecting member without adversely affecting the gripping means 140. The internal end of the connecting means 114" proximate the terminal portion 18 of the second end 16" of the stent member is formed to have a flange 166 having a circumference in the shape of the housing 60'. Typically, the circumferential shape would be circular. A disk member 168 is connected loosely by a plurality of pins 170, each extending through the flange 166 and through an annular bore 172 formed in the disk member 168. A generally conical axial bore is formed in the disk member 168 to allow for the full opening of the jaws of the gripping means 140. The inner surface of the comical bore 169 serves as a bearing surface against the arms of the yokes 146 and 148 when the connecting member 114" is moved to extend the stent member 12" away from the stent placement member 52.

Because of the manner in which the flange 166 of the connecting member 114" is connected to the disk member 168, the connecting member 114" may be rotated without rotating the disk member 168. Preferably, the pushrod 162 has a diameter to provide sufficient clearance within the axial bore 115 to avoid friction and twisting of the gripping means which may result in unwanted twisting of the stent member.

The embodiments of the anastomosis apparatus according to the present invention as illustrated in FIGS. 12 through 15 provide for a more precise placement of the stent member 12" with respect to the stent placement member 52 within the vessel stumps 120 and 200. If desired, as explained above, calibrations may be provided for the rack and pinion adjusting arrangement shown in FIG. 12 or for the screw adjustment arrangement illustrated in FIG. 13.

In view of this disclosure, it will be appreciated that the dissolvable stent for mammalian anastomoses according to the present invention may be used to provide intraluminal support during anastomosis procedures and to provide compression forces to hold the introflected portions of the vessel stumps in an engaged position for only the time necessary to permit the application and solidification or curing of a biocompatible sealant, rather than providing a conventional anastomosic stent which maintains compressive forces on the engagement region for considerably longer periods of time as also occurs with mechanical suturing devices and pressure suturing devices in general. Such reduced compression time helps to avoid ischemia, necrosis or fibrosis with resulting substenosis or stenosis, or even eventual micro- or macroperforation which are typical complications associated with conventional mechanical and BAR anastomosis stents and techniques.

The stent of the present invention has major advantages over conventional mechanical and pressure suturing techniques and the BAR. An important improvement is that the stent may be withdrawn and replaced (for example, if there is a sizing error, poor technique, etc.) continuously at the same site without resectioning or damaging the existing stump margins. This is not possible for either mechanical sutures or the BAR which cannot be replaced once in place without resectioning the vessel both above and below the staples (mechanical) or BAR device, thus shortening the two stumps (which is not always possible or desirable) and requiring additional surgical procedures. The stent can be reduced in size at the surgical table by using a surgical blade or sanding device to better match the lumen and stent diameters; this is not possible for either the BAR or for mechanical sutures where another size device must be chosen, which may or may not be appropriate. Further, where unsuccessful initial efforts using prior art techniques must be repeated, the total cost increases.

The stent's unique advantages over the BAR are that it can be used in the small intestine with an intact ileocecal valve, it can be used with any thickness of vessel stumps and it has no possibility of becoming plugged by feces in lower colon or rectal applications, since it generally dissolves within about 30 to about 90 minutes, depending on its chemical components.

In addition, the stent according to the present invention is substantially completely dissolvable in mammalian bodily fluids and is constructed of a biocompatible material, thereby avoiding the implantation of foreign objects in vivo, avoiding possible blockage problems associated with conventional mechanical and BAR anastomosis techniques and virtually eliminating problems associated with the passing of intact BAR devices or their fragments. The reinforcing means provide additional strength to the stent of the present invention, reducing the number of broken stents needing replacement and allowing partially and even completely broken stents to have sufficient structural integrity for use in anastomosis procedures.

Further, using the anastomosic stent according to the present invention, a significantly improved anastomosis procedure may be performed allowing the removal of pursestring sutures which, in conventional anastomosis procedures, typically causes increased necrosis, ischemia and edema. The removal of such purse-string sutures is strongly preferred because it eliminates any foreign body from the site of the surgical procedure, which cannot be said for any other techniques which all leave absorbable or non-absorbable suture, metal staples or the BAR device itself.

Still further, the anastomosis apparatus according to the present invention allows for improved anastomosis procedures especially in those areas that are hard to reach and where positioning and manipulation of hands and surgical devices is difficult. The use of the anastomosis apparatus also obviates unnecessary manipulation of the vessel, reducing ischemia, for example. Another primary advantage of the stent of the present invention is the total absence of long-term tissue pressure when it is used. This is a significant improvement over all pressure anastomosis techniques (sutures, mechanical stapler, BAR, etc.) which by virtue of their closure, compromise the vascular supply (large and/or small vessel). This does not occur with the stent or stent placement device of the present invention, as both only clamp the vessel stumps together for a total of about ten minutes, typically, after which pressure is released and dissolution of the components continues. The total time preferably is divided into two periods, thus allowing revascularization in the interval.

The invention will now be illustrated in further detail by reference to the following specific, non-limiting examples. While the examples discussed below were performed on intestinal vessels, it will be readily appreciated by one skilled in the art that the present invention may be readily modified for anastomoses of other vessel organs.

EXAMPLE 1

A two piece intestinal stent intended for use in intestinal anastomoses in pigs was prepared from a sucrose and water mixture. Granular sucrose was added to heated water in a beaker until the mixture was approximately a 2:1 by weight ratio of sucrose to water. The mixture was heated to approximately 250° F. and stirred until the sucrose dissolved. The sucrose and water mixture was slowly poured into molds formed from 0.01 millimeter sheets of aluminum. Some of the molds had preinserted reinforcing members in the form of absorbable suture lengths. The stent intended for use in the colon was initially formed in three parts: (1) the second end of the male member or shaft-shaped member measured approximately 40 millimeters in length, 17 millimeters in diameter and appeared generally circular in cross-section; (2) the first end of the male member measuring approximately 27 millimeters in diameters at its largest point and tapering distally to a diameter of approximately 17 millimeters; and (3) a corresponding female member having the same dimensions as the first end of the male member. Stents intended for use in the small intestine had correspondingly smaller dimensions.

The water and sucrose mixture was poured into the shaft molds, some of which had the reinforcing members already inside and cooled until the shaft was hardened. The sucrose and water mixture was then poured into the male and female member molds, some of which had the reinforcing members attached inside. Approximately 3–5 minutes after pouring the mixture into the male member mold, the hardened shaft member was inserted approximately 20 millimeters into the semi-hardened male member mold and stabilized vertically while hardening continued. A hollow or solid 18 millimeter diameter tube was inserted into the female member mold to form an inner cavity having a circumference for at least partially receiving the second end of the male member. The hollow or solid tube was twisted occasionally to keep it from becoming solidified in the female member mold. When semi-hardening of the female member mold was observed (marked by the formation of large crystals or free rotation of the hollow or solid tube without deformation of the surrounding semi-hardened stent upon rotation of the hollow tube), the tube was withdrawn. After cooling, portions of the reinforcing suture lengths extending from the stent were trimmed. Then the stents were stored at 4° C., but they can also be stored at room temperature.

EXAMPLE 2

80 female Landrace pigs weighing approximately 25 to 35 kilograms were used to perform 80 anastomoses—40 with the dissolvable stent according to Example 1 of the present invention and fibrin sealant; 40 controls with 4-O (colon) and 5-O (small intestine) reabsorbable sutures. Premedication included a mixture of atropine (i.m. 0.01 mg/kg of body weight) and ketamine (2.5 mg/kg). Anesthesia was induced using a mixture of halothane (0.5%–1.0%) and $NO_2$ (70%) with remaining percentage $O_2$ using a face mask with spontaneous breathing. Intravenous infusion (auricular vein) of 5% glucose (300–500 ml) or physiologic solution was employed for the length of the operation to permit intravenous drug administration (ketamine, e.g.) and atropine when needed.

The anastomosis procedure began with a mid-line abdominal incision long enough to localize the intestinal loop to be worked on. The segment of the intestine where the anastomosis was to be performed was then mobilized. Cutting and cauterization of the intestine walls were done slowly and layer-by-layer to reduce the phenomenon of bulging tissue. Purse-string sutures were inserted above and below the anastomosis site. Using a stent prepared according to the procedure of Example 1, the stent members were inserted into the stumps. The second end of the male member of the stent was then inserted into the female member of the stent and the two purse-string sutures were tightened to introflect the stump edges onto the second end of the male member and to hold them in position on the male stent shaft. The stent was then closed to compress the introflected edges of the stumps together using pressure from the thumb and index finger. TISSUCOL™ sealant was then applied and pressure was applied for 2–4 minutes. After 6 minutes, the purse-string sutures were removed and a second layer of sealant was applied to cover the suture holes. After a second waiting period of 6–7 minutes for the sealant to cure, the stent was then gently pushed away from the anastomosis to check the patency of the lumen and to reduce circumferential and vascular pressure at the anastomosis.

The animals were brought out of anesthesia by ceasing halothane administration approximately 10 minutes before the end of the operation and lowering the $NO_2$ level and then stopping it at closure. The animals were then maintained on $O_2$ until the first signs of movement. Postoperatively, the animals were starved for the first postoperative day and received a mush (regular chow mix with water) the second day. Regular feeding was resumed on the third postoperative day.

There were no intraoperative deaths and no postoperative deaths. No unusual changes in bowel function were noted and there were no significant clinical differences between those animals undergoing the anastomosis procedure in accordance with the present invention versus the control procedures. Macroscopic examination of the pigs at 7, 14, 21, 30, 45, 60 days and at 4, 6, 8, 10 and 18 months indicated no significant difference in adhesion or edema occurrence at the anastomosis sites in the experimental pigs versus the control pigs, indicating the success of the experimental procedures. Further, during macroscopic inspection, the anastomosis lines were often difficult to see in the non-control animals without the aid of markers (sutures) on the intestinal serosa or a microscope at 21 and 30 days and were not always found at later sacrifice times. Microscopic examination showed less occurrence of granulation tissue in the experimental pigs than in the control pigs. The decreased granulation tissue occurrence in the experimental pigs indicated fewer infections at the anastomosis site up to 30 days. It is believed that this is due to the non-compromised vascular supply of the stump edges and to the absence of foreign bodies, such as sutures, in the anastomosed vessels. After 30 days, the test and control samples were similar except when the sutures had trapped part or parts of the stump margin. The lack of lumen stricture and absence of signs of surgery, especially in the long-term animals (2 months to 18 months), were striking.

EXAMPLE 3

Eight (8) Landrace pigs were used to perform eight (8) anastomoses using the anastomosis apparatus described above—six (6) in the small intestine and two (2) in the low rectum. Preanesthesia and anesthesia procedures were identical to the procedures described above in Example 2. In addition, the surgical procedures described above in Example 2 were followed with appropriate alterations in location for the anastosomis site. The main difference in surgical procedures was the opening and closing of the enterotomy used to insert the anastomosis apparatus for the small intestine anastomoses and a transanal approach associated with the rectal procedures. Wash-out with saline, closing and post operative care were as described in Example 2.

For the low rectal procedure, the laparotomy was lower, in the area of the bladder, to enable reaching the low rectum and was combined with a transanal approach for the stent placement device. There was a preliminary wash-out of the rectum using a rectal tube to flush with urologic solution. The cephalad stump was clamped before sectioning the low rectum to prevent fecal leakage. The tract from the sectioned rectum to the anus was washed again with urologic solution. After these preparative procedures, the apparatus 50 of FIGS. 6–8 was inserted transanally and positioned as described above. Introflection of the stump edges, and application of TISSUCOL™ sealant were performed as described in Example 2.

There were no intraoperative deaths and no postoperative deaths. No unusual changes in bowel function were noted and the animals exhibited generally excellent health at time of sacrifice or observation at 30 days and 60 days.

The present invention may be embodied in other specific forms without departing from the spirit or essential attributes thereof and, accordingly, reference should be made to the appended claims, rather than to the foregoing specification as indicating the scope of the invention.

I claim:

1. A method of surgical mammalian vessel anastomosis connecting a first vessel stump having a generally annular opening to a second vessel stump having a generally annular opening using an anastomosis apparatus comprising a stent member for receiving the first vessel stump, the stent member having a first end with a first circumference and a second end with a second circumference smaller than the first circumference, the stent member being made of a biocompatible, non-toxic material which substantially completely dissolves in mammalian bodily fluids, and a removable stent placement member for insertion through a second vessel stump, the stent placement member having an outer circumference substantially the same as the first circumference of the stent member and having a receiving portion with an inner circumference for at least partially receiving the second end of the stent member, the stent member and the receiving portion of the stent placement member being substantially axially aligned when the second end of the stent member is received by the stent placement member, the anastomosis apparatus further comprising a connecting member secured to the stent member and compression retaining means attached to the stent placement member and functionally attached to the connecting member for applying and holding a compressive force for retaining the second end of the stent member at least partially within the receiving portion of the stent placement member, the method comprising the steps:
   (a) circumferentially inserting a first purse-string suture into the first vessel stump and circumferentially inserting a second purse-string suture into the second vessel stump, the first and second purse-string sutures being positioned proximate edges of the first and second vessel stumps;
   (b) placing the stent member at least partially within the receiving portion of the stent placement member;
   (c) inserting the stent member and stent placement member through an opening in the second vessel stump remote from the generally annular opening of the second vessel stump until the stent member extends at least partially through the generally annular opening of the second vessel stump;
   (d) inserting the first end of the stent member into the generally annular opening of the first vessel stump;
   (e) tightening the purse-string sutures to annularly introflect the edges of the first and second vessel stumps onto the second end of the stent member;
   (f) applying a compressive force to the stent member within the receiving portion of the stent placement member to cause the annularly introflected edge of the first vessel stump to engage the annularly introflected edge of the second vessel stump to form an engagement region between the stent member and the stent placement member with a clamping force sufficient to maintain the edges of the stumps in annular engagement;
   (g) applying a biocompatible sealant capable of curing in minutes to external surfaces of the first and second vessel stumps to substantially completely cover the stumps in the annular engagement region;
   (h) removing the purse-string sutures from the first and second vessel stumps; and
   (i) promptly after the sealant cures, releasing the compressive force between the stent member and the stent placement member.

2. A method of surgical mammalian vessel anastomosis connecting a first vessel stump having a generally annular opening to a second vessel stump having a generally annular opening using an anastomosis apparatus comprising a stent member for receiving the first vessel stump, the stent member having a first end with a first circumference and a second end with a second circumference smaller than the first circumference, the stent member being made of a biocompatible, non-toxic material which substantially completely dissolves in mammalian bodily fluids, and a removable stent placement member for insertion through a second vessel stump, the stent placement member having an outer circumference substantially the same as the first circumference of the stent member and having a receiving portion with an inner circumference for at least partially receiving the second end of the stent member, the stent member and the receiving portion of the stent placement member being substantially axially aligned when the second end of the stent member is received by the stent placement member, the anastomosis apparatus further comprising a connecting member secured to the stent member and compression retaining means attached to the stent placement member and functionally attached to the connecting member for applying and holding a compressive force for retaining the second end of the stent member at least partially within the receiving portion of the stent placement member, the method comprising the steps:
   (a) circumferentially inserting a first purse-string suture into the first vessel stump and circumferentially inserting a second purse-string suture into the second vessel stump, the first and second purse-string sutures being positioned proximate edges of the first and second vessel stumps;
   (b) placing the stent member at least partially within the receiving portion of the stent placement member;
   (c) inserting the stent member and stent placement member through an opening in the second vessel stump remote from the generally annular opening of the second vessel stump until the stent member extends at least partially through the generally annular opening of the second vessel stump;
   (d) inserting the first end of the stent member into the generally annular opening of the first vessel stump;
   (e) tightening the purse-string sutures to annularly introflect the edges of the first and second vessel stumps onto the second end of the stent member; and
   (f) applying a compressive force to the stent member within the receiving portion of the stent placement member to cause the annularly introflected edge of the first vessel stump to engage the annularly introflected edge of the second vessel stump to form an engagement region between the stent member and the stent placement member with a clamping force sufficient to maintain the edges of the stumps in annular engagement;
   (g) applying a biocompatible sealant capable of curing in minutes to external surfaces of the first and second vessel stumps to substantially completely cover the stumps in the annular engagement region;
   (h) removing the purse-string sutures from the first and second vessel stumps;
   (i) applying a biocompatible sealant to cover any holes in the vessel stumps remaining after removing the purse-string sutures in step (h); and
   (j) promptly after the sealant cures, releasing the compressive force between the stent member and the stent placement member.

3. A method of surgical mammalian vessel anastomosis connecting a first vessel stump having a generally annular opening to a second vessel stump having a generally annular opening using an anastomosis apparatus comprising a stent member for receiving the first vessel stump, the stent member having a first end with a first circumference and a second end with a second circumference smaller than the first circumference, the stent member being made of a biocompatible, non-toxic material which substantially completely dissolves in mammalian bodily fluids, and a removable stent placement member for insertion through a second vessel stump, the stent placement member having an outer circumference substantially the same as the first circumference of the stent member and having a receiving portion with an inner circumference for at least partially receiving the second end of the stent member, the stent member and the receiving portion of the stent placement member being substantially axially aligned when the second end of the stent member is received by the stent placement member, the anastomosis apparatus further comprising a connecting member secured to the stent member and compression retaining means attached to the stent placement member and functionally attached to the connecting member for applying and holding a compressive force for retaining the second end of the stent member at least partially within the receiving portion of the stent placement member, the method comprising the steps:
(a) circumferentially inserting a first purse-string suture into the first vessel stump and circumferentially inserting a second purse-string suture into the second vessel stump, the first and second purse-string sutures being positioned proximate edges of the first and second vessel stumps;
(b) placing the stent member at least partially within the receiving portion of the stent placement member;
(c) inserting the stent member and stent placement member through an opening in the second vessel stump remote from the generally annular opening of the second vessel stump until the stent member extends at least partially through the generally annular opening of the second vessel stump;
(d) inserting the first end of the stent member into the generally annular opening of the first vessel stump;
(e) tightening the purse-string sutures to annularly introflect the edges of the first and second vessel stumps onto the second end of the stent member; and
(f) applying a compressive force to the stent member within the receiving portion of the stent placement member to cause the annularly introflected edge of the first vessel stump to engage the annularly introflected edge of the second vessel stump to form an engagement region between the stent member and the stent placement member with a clamping force sufficient to maintain the edges of the stumps in annular engagement;
(g) applying a biocompatible sealant capable of curing in minutes to external surfaces of the first and second vessel stumps to substantially completely cover the stumps in the annular engagement region;
(h) removing the purse-string sutures from the first and second vessel stumps;
(i) promptly after the sealant applied in step (g) at least partially cures sufficient to bind the vessel stumps together without the compressive force, temporarily releasing the compressive force between the stent member and the stent placement member;
(j) applying a biocompatible sealant to cover any holes in the vessel stumps remaining after removing the purse-string sutures in step (h); and
(k) again applying a compressive force between the stent member and the stent placement member for only such time as is necessary for the sealant applied in step (j) to cure.

4. A method of surgical mammalian vessel anastomosis connecting a first vessel stump having a generally annular opening to a second vessel stump having a generally annular opening using an anastomosis apparatus comprising a stent member for receiving the first vessel stump, the stent member having a first end with a first circumference and a second end with a second circumference smaller than the first circumference, the stent member being made of a biocompatible, non-toxic material which substantially completely dissolves in mammalian bodily fluids, and a removable stent placement member for insertion through a second vessel stump, the stent placement member having an outer circumference substantially the same as the first circumference of the stent member and having a receiving portion with an inner circumference for at least partially receiving the second end of the stent member, the stent member and the receiving portion of the stent placement member being substantially axially aligned when the second end of the stent member is received by the stent placement member, the anastomosis apparatus further comprising a substantially rigid connecting member secured to the stent member and compression retaining means attached to the stent placement member and functionally attached to the connecting member for applying and holding a compressive force for retaining the second end of the stent member at least partially within the receiving portion of the stent placement member, and releasable gripping means for releasably gripping the stent member, the releasable gripping means being normally spring biased in a closed, gripping condition, the method comprising the steps:
(a) circumferentially inserting a first purse-string suture into the first vessel stump and circumferentially inserting a second purse-string suture into the second vessel stump, the first and second purse-string sutures being positioned proximate edges of the first and second vessel stumps;
(b) placing the stent member at least partially within the receiving portion of the stent placement member;
(c) inserting the stent member and stent placement member through an opening in the second vessel stump remote from the generally annular opening of the second vessel stump until the stent member extends at least partially through the generally annular opening of the second vessel stump;
(d) inserting the first end of the stent member into the generally annular opening of the first vessel stump;
(e) tightening the purse-string sutures to annularly introflect the edges of the first and second vessel stumps onto the second end of the stent member; and
(f) applying a compressive force to the stent member within the receiving portion of the stent placement member to cause the annularly introflected edge of the first vessel stump to engage the annularly introflected edge of the second vessel stump to form an engagement region between the stent member and the stent placement member with a clamping force sufficient to maintain the edges of the stumps in annular engagement.

5. The method according to claim 4 wherein the anastomosis apparatus further comprises a driving means for driving the connecting means axially within the apparatus.

6. The method according to claim 1, wherein the biocompatible sealant is fibrin glue.

7. The method according to claim 1, wherein one of the first and second vessel stumps is an intestinal stump.

8. The method according to claim 7, wherein the other of the first and second vessel stumps is an esophogeal stump.

9. The method according to claim 7, wherein the other of the first and second vessel stumps is a gallbladder stump.

10. The method according to claim 1 wherein the connecting member of the anastomosis apparatus is substantially rigid.

11. The method according to claim 10 wherein the anastomosis apparatus further comprises a driving means for driving the connecting means axially within the apparatus.

12. The method according to claim 11 wherein the driving means of the anastomosis apparatus comprises a screw arrangement whereby the connecting means has a threaded portion which mates with a threaded bushing member on a housing of the apparatus, whereby rotation of one of the connection means and the bushing member causes axial movement of the connecting member.

13. The method according to claim 10 wherein the anastomosis apparatus further comprises releasable gripping means for releasably gripping the stent member.

14. The method according to claim 5 wherein the driving means of the anastomosis apparatus comprises a screw arrangement whereby the connecting means has a threaded portion which mates with a threaded bushing member on a housing of the apparatus, whereby rotation of one of the connecting means and the bushing member causes axial movement of the connecting member.

* * * * *